United States Patent [19]

Toda et al.

[11] 4,026,277

[45] May 31, 1977

[54] BLOOD PRESSURE MEASURING APPARATUS

[75] Inventors: Atsushi Toda, Toyonaka; Yoshifumi Matsuoka, Yamatotakada; Koichi Shigematsu, Kawanishi, all of Japan

[73] Assignee: Matsushita Electric Industrial Co., Ltd., Osaka, Japan

[22] Filed: Apr. 7, 1975

[21] Appl. No.: 565,371

[30] Foreign Application Priority Data

| Apr. 12, 1974 | Japan | 49-41122 |
| Apr. 12, 1974 | Japan | 49-41123 |
| Apr. 16, 1974 | Japan | 49-43151 |
| Apr. 18, 1974 | Japan | 49-44073 |
| Apr. 18, 1974 | Japan | 49-44075 |
| Apr. 18, 1974 | Japan | 49-44288[U] |

[52] U.S. Cl. .................. 128/2.05 A; 128/2.05 M
[51] Int. Cl.² ............................. A61B 5/02
[58] Field of Search ............. 128/2.05 A, 2.05 D, 128/2.05 G, 2.05 P, 2.05 Q, 2.05 R, 2.05 S, 2.05 M, 2 K; 235/92 EA

[56] References Cited

UNITED STATES PATENTS

| 3,140,710 | 7/1964 | Glassner et al. | 128/2.05 S |
| 3,280,817 | 10/1966 | Jorgensen et al. | 128/2.05 S |
| 3,308,811 | 3/1967 | Gillette et al. | 128/2.05 M |
| 3,450,131 | 6/1969 | Vogt | 128/2.05 A |
| 3,581,735 | 6/1971 | Gentner | 128/2.05 S X |
| 3,605,723 | 9/1971 | King et al. | 128/2.05 M |
| 3,791,378 | 2/1974 | Hochberg et al. | 128/2.05 M |
| 3,814,083 | 6/1974 | Fletcher et al. | 128/2.05 S |
| 3,841,314 | 10/1974 | Page | 128/2.05 P |
| 3,905,354 | 9/1975 | Lichowsky | 128/2.05 M |
| 3,978,848 | 9/1976 | Yen et al. | 128/2.05 M |

FOREIGN PATENTS OR APPLICATIONS

| 1,466,829 | 6/1969 | Germany | 128/2.05 R |
| 2,039,241 | 2/1972 | Germany | 128/2.05 A |
| 1,216,241 | 12/1970 | United Kingdom | 128/2.05 M |

*Primary Examiner*—Richard C. Pinkham
*Assistant Examiner*—Vance Y. Hum
*Attorney, Agent, or Firm*—Stevens, Davis, Miller & Mosher

[57] ABSTRACT

A blood pressure measuring apparatus in which an output of a microphone capable of detecting the Korotkoff sounds is directed to a first band-pass filter of 5 to 30 Hz and a second band-pass filter of 40 to 200 Hz, and the presence or absence of an output from the second band-pass filter is counted by a counter circuit, whereby the maximum blood pressure is indicated when the counter is set to one state and the minimum blood pressure is indicated when the counter is set to the other state.

8 Claims, 13 Drawing Figures

BLOOD PRESSURE MEASURING APPARATUS

The present invention relates to an indirect electrical blood pressure measuring apparatus.

It has been well known that when a brachial artery is squeezed by a cuff to temporarily cease the flow of blood and then squeezing pressure by the cuff is gradually decreased, blood flow sound called the Korotkoff sounds is generated in the arterial wall when the blood again starts to flow. In the auscultatory method, the cuff pressure at which the Korotkoff sounds are first generated in decreasing the pressure is decided as a maximum blood pressure. The Korotkoff sounds are continuously generated with the decrease of the cuff pressure until the blood flow starts to flow continuously. The pressure at which the Korotkoff sounds disappear is decided as a minimum blood pressure.

In an automatic electronic blood pressure measuring apparatus, the times of appearing and disappearing of the Korotkoff sounds are detected to measure and indicate the cuff pressures at those moments. The Korotkoff sounds are usually picked up by a microphone. Since a signal level thereof is very low and readily influenced by external noise, it has been a difficult problem in the prior art automatic blood pressure measuring apparatus to separate the Korotkoff sounds from the noise.

The present invention aims to eliminate the difficulties encountered in the prior art apparatus.

It is an object of the present invention to provide a blood pressure measuring apparatus which enables separation of the noise from the Korotkoff sounds in sphygmus signal to allow accurate detection of blood pressure.

The above and other objects, features and advantages of the present invention will become more apparent from the following detailed description of the preferred embodiment of the present invention when taken in conjunction with the accompanying drawings, in which.

Figure 1:
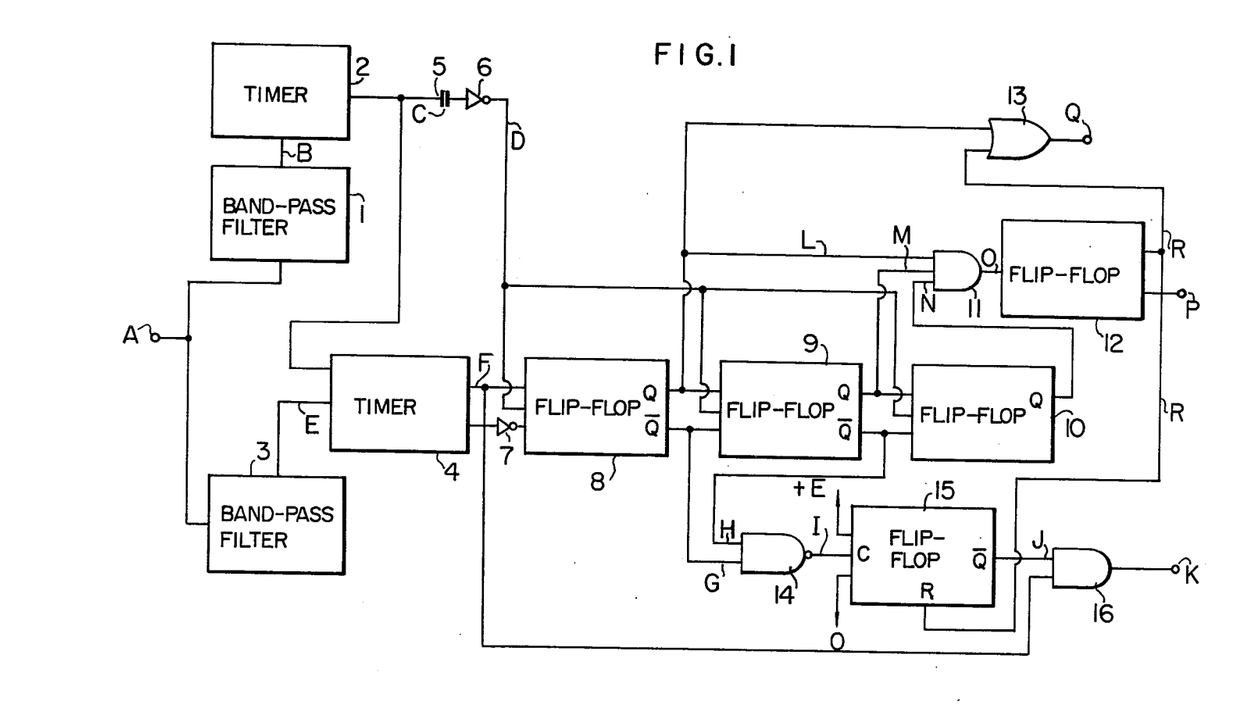
FIG. 1 shows a block diagram of one embodiment of a blood pressure measuring apparatus in accordance with the present invention.

FIG. 1 shows one embodiment of the present invention. In FIG. 1, the letter A designates an output terminal of a microphone for detecting the Korotkoff sounds. The reference numeral 1 designates a bandpass filter which passes frequency components of a sphygmus wave, for example 5 to 30 Hz. The numeral 2 designates a timer which generates a pulse signal of a predetermined duration, for example, a monostable multivibrator which is responsive to an output from the filter 1 to be switched to an unstable state for a time period of the sphygmus wave duration, approximately 100 to 400 m sec. The numeral 3 designates a bandpass filter which passes frequency components of the Korotkoff sounds, for example 40 to 200 Hz. The numeral 4 designates a timer which may be constituted by a monostable multivibrator which is similar to the multivibrator 2 and which receives an output of the filter 3 only during the switched state of the multivibrator 2 to be switched to an unstable state. The duration of switching state is substantially equal to or longer than that of the multivibrator 2. Hereinafter, the description is made as to the embodiment in which the timer circuit is constituted by a monostable multivibrator. The output of the multivibrator 2 is differentiated by a capacitor 5 and an inverter 6 and then it is applied as a clock pulse to a suitable counter or a shift register consisting of flip-flops 8, 9 and 10. An input of the shift register is coupled to an output of the monostable multivibrator 4. The Q outputs of the respective stages of the shift register are ANDed at an AND gate 11, an output of which is used to activate a flip-flop 12. An output of the flip-flop 12 and the output Q of the first stage 8 of the shift register are ORed at an OR gate 13. The Q outputs of the first stage 8 and the second stage 9 of the shift register are connected to a NAND gate 14, an output of which is used as a set signal to a flip-flop 15. The output of the flip-flop 12 is used as a reset signal to the flip-flop 15 so that the flip-flop 15 remains in its reset state until the flip-flop 12 is set. An output $\overline{Q}$ of the flip-flop 15 and the output of the multivibrator 4 are applied to an AND gate 16, an output of which is taken out as a system output.

Figure 2:
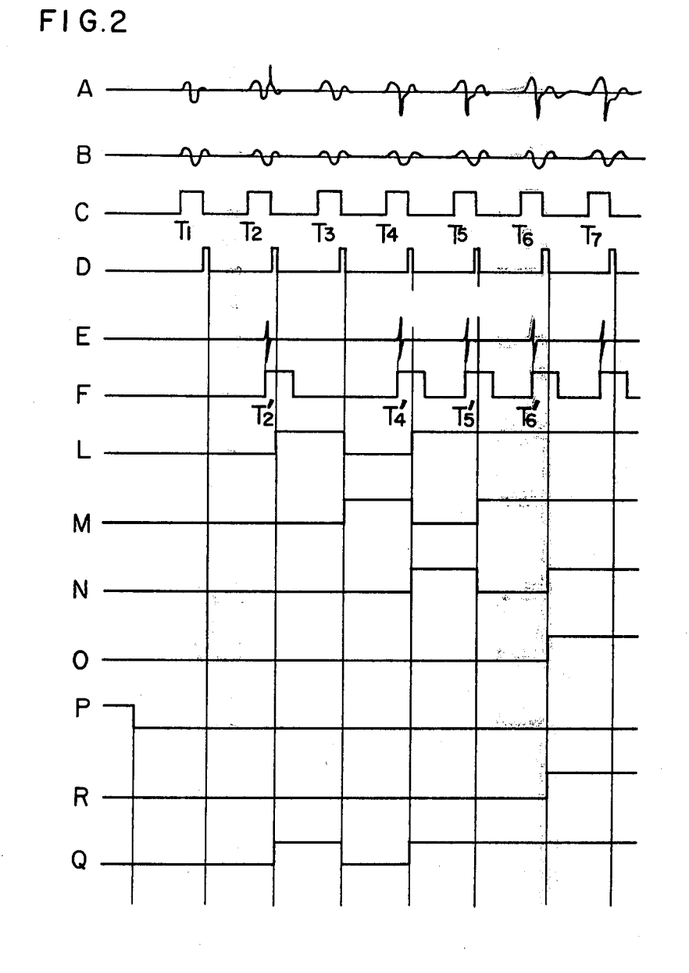
FIGS. 2 and 3 show waveforms at various points in the apparatus shown in FIG. 1.

The operation of the above system is now explained. FIG. 2 shows waveforms at various points in the system when the cuff pressure, which has once been raised above a maximum blood pressure, is gradually decreased with time. Waveform A at the output of the microphone is a composite waveform of the sphygmus sounds and the Korotkoff sounds. The sphygmus sounds B are separated by the filter 1 while the Korotkoff sounds E are separated by the filter 3. When the microphone is wrapped in a cuff the microphone picks up the change in the artery pressure, which occurs corresponding with a pulse and then is extracted as sphygmus sounds by the filter 1 as shown in the waveform B. Therefore, for each sphygmus wave a square wave is produced as shown in a waveform C by $T_1$ to $T_7$, which is then differentiated to produce a waveform D. Assuming that a noise in the frequency range of the Korotkoff sounds is generated at time $T'_2$, the monostable multivibrator 4 is activated and the output shown in F sets the output of the flip-flop 8 to a high level as shown in L at the clock input of D. This causes the Q output of the OR gate 13 to go high. The Q-high output indicates the maximum blood pressure which indicates a momentarily latched cuff pressure at that moment. Thereafter, at time $T_3$, the waveform D produces a next clock input. However, since the Korotkoff sounds do not exist at this moment the waveform F remains at its low level and the output waveform L of the flip-flop 8 is set to the low level. Therefore, the output of the OR gate 13 again assumes its low level to release latching for the indication of the maximum blood pressure to allow actual cuff pressure to be indicated. At the time $T_4'$, when the Korotkoff sound as shown in the waveform E is generated, the waveform L is set to high level as in the case of $T_2'$ and the output waveform Q of gate 13 is also set to high level for locking the indication of the cuff pressure. Then, at the time $T_5'$, when a Korotkoff sound is generated, the waveform L remains at its high level and the output waveform M of the flip-flop 9 is set to high level at a clock pulse in the waveform D because the output of its preceeding stage is at high level. At the time $T_6'$, when the Korotkoff sound is generated, the waveforms L and M remain at their high levels and the output waveform N of the flip-flop 10 is set to its high level at a clock pulse input from the waveform D in response to the output waveform M of the preceding stage. Then, all of the three output waveforms L, M and N are at high level so that the output waveform O of the AND gate 11 assumes a high level to set the output waveform R of the flip-flop 12 to a high level. As a result, the output waveform Q of the OR gate 13 remains at its high level to hold the cuff pressure at the moment of time $T_4'$. This allows the indication of the maximum blood pressure.

In the present embodiment, when three successive Korotkoff sounds appear in synchronism with the sphygmus, the cuff pressure at the moment of the first Korotkoff sound is detected as the maximum blood pressure. It should be understood that two successive sounds or more than three successive sounds may be employed to obtain the same effect with the accuracy being increased with the number of stages. When the system is to be made ready for the next measurement, a reset pulse shown in the waveform P may be applied to input P (FIG. 1) to reset flip-flop 12.

In this manner the present invention uses the sphygmus sounds to discriminate the Korotkoff sounds such that when a sphygmus sound appears but no Korotkoff sound appears as at time $T_3$, the blood pressure indication which has once held as the maximum blood pressure indication is cleared to ready for the reception of the next Korotkoff sound. Accordingly, the present system allows high accuracy and reliable measurement even for a person whose intervals between sphygmuses are somewhat irregular.

Figure 3:
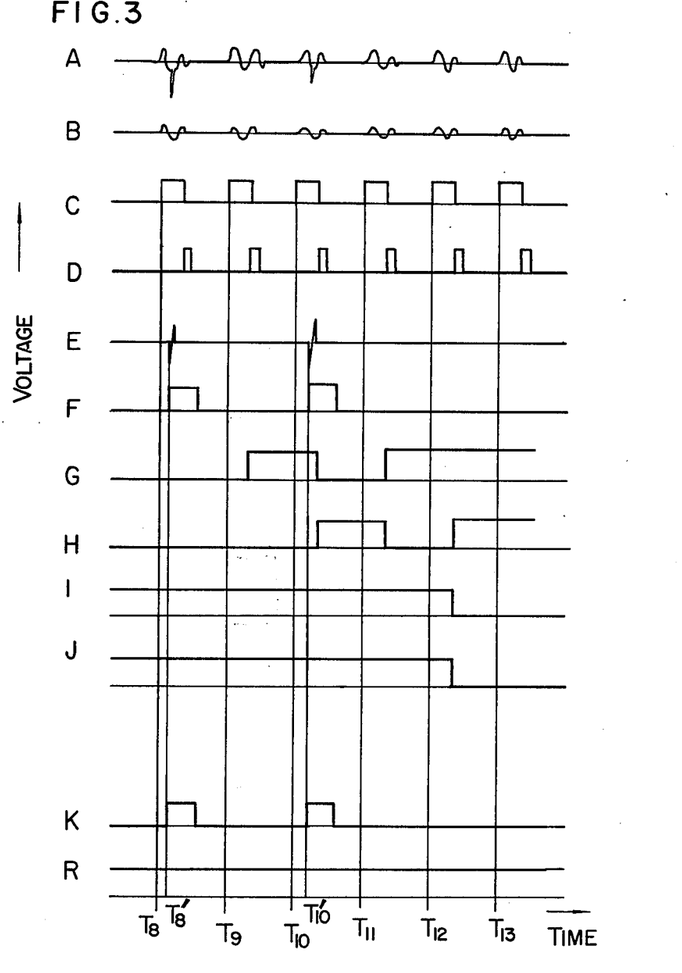

The measurement of the minimum blood pressure is now explained. In FIG. 3, A to K and R designate waveforms at various points in the system shown in FIG. 1, as in FIG. 2. FIG. 3 shows the change of status with time where the cuff pressure is gradually decreased from a pressure at which the Korotkoff sounds are generated until they disappear. The waveforms A to F are same as those shown in FIG. 2. Assuming that the Korotkoff sounds are successively generated in synchronism with the sphygmus until time $T_8'$, the multivibrator 4 is activated for each occurence of the Korotkoff sounds, and in response thereto the flip-flops 8 and 9 are set to high level at the clock signal D; the waveforms G and H thus remain at their low level. If the Korotkoff sound is accidently missed at time $T_9$ by missphygmus, the multivibrator 4 is not activated at that moment and the flip-flop 8 is set with the output G at high level. Since the level of the flip-flop 8 is shifted to the flip-flop 9 the output H remains at low level and the output I remains at high level. Thus, at the time $T_{10}'$, if the Korotkoff sound again appears, the output G of the flip-flop 8 again assumes low level while the output I remains unchanged.

When the Korotkoff sounds do not appear at successive times $T_{11}$ and $T_{12}$, the outputs G and H both assume high level and the output I assumes low level so that the flip-flop 15 is set with the output I being at low level. The AND gate 16 serves to indicate the pressure value and during high level state of the output J it renders the output K high level when a Korotkoff sound appears and the waveform F is at high level. Therefore, only when the output K is at high level, a pressure indication input is gated and only when a Korotkoff sound appears the pressure at that moment is indicated, and when the Korotkoff sounds do not appear successively the cuff pressure at the moment of the last occured Korotkoff sound is indicated. As a result, when the waveform J assumes low level, the output K remains at its low level and the minimum blood pressure is established. In the present embodiment, the minimum blood pressure is established when two successive Korotkoff sounds in synchronism with the sphygmus sounds are missed. Missing of more than two successive Korotkoff sounds may be used to determine the minimum blood pressure by coupling the output $\bar{\theta}$ of the flip-flop 10, which is connected following to the flip-flop 9, to the NAND gate 14 together with the waveforms H and G.

In this manner the present invention determines the minimum blood pressure by the presence or absence of the Korotkoff sounds which are in synchronism with the sphygmus sounds. Thus, the present system allows accurate measurement of blood pressure, which is independent of time intervals of sphygmuses and personal characteristic. Further since the minimum blood pressure is determined by the absence of two or more successive Korotkoff sounds, the present system allows the measurement of blood pressure for a person whose sphygmus is irregular.

While the monostable multivibrators 2 and 4 are used as timers in the embodiment of FIG. 1, any other circuit which is functionally similar may be used as well. For example, flip-flops having time limit characteristic in their set and reset signals may be equally employed.

A modified filter circuit which incorporates an AGC (automatic gain control) circuit and which may be used in place of the filter 1 for detecting the sphygmus sounds is now explained in detail. Since the present system uses the sphygmus sounds as references for determination, the detection of the sphygmus sounds should be reliably performed.

However, the sphygmus varies in magnitude depending on personal characteristic, and because of body movement or heart disease or the like, a waveform which has similar frequency components as those of the sphygmus wave is observed at periods other than regular sphygmus wave occuring periods.

Figure 4:
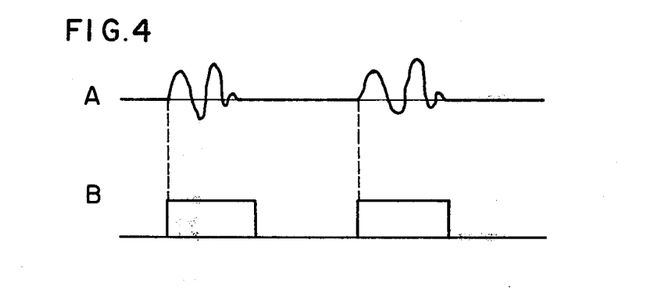
FIGS. 4 and 5 show sphygmus waves and output waveforms of a timer.
Figure 5:
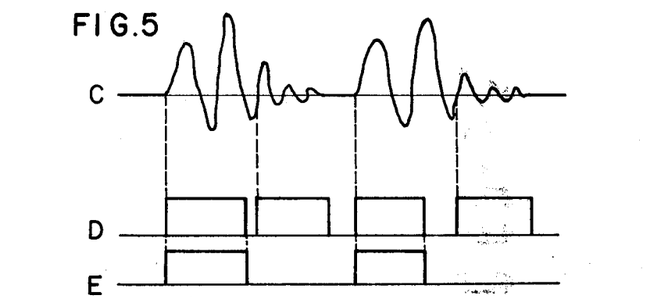

Referring to FIGS. 4 and 5, FIG. 4 shows the case of a normal person whereas FIG. 5 shows the case of a person whose sphygmus wave is very intensely detected. At A and C there are illustrated output waveforms of the band-pass filter 1 of FIG. 1 in the both cases. Waveforms shown at B and D are outputs of the timer 2. In the case of FIG. 4, one output is generated by the timer 2 for each sphygmus wave and normal output waveforms are obtained. However, in the case of FIG. 5, since the duration of one sphygmus wave is long, the timer 2 is subsequently activated by the next signal after the timer 2 has finished one operational period. Thus, the timer 2 is activated twice for each one sphygmus wave and generates two successive output waveforms as shown at D. However, since the Korotkoff sounds are contained only in the first output of the successive two outputs shown at D, even where the Korotkoff sounds are generated, the sphygmus wave is detected only alternately in the successive two outputs of the timer, resulting in a possible trouble in accurate decision by the counter circuit.

In the modified filter circuit, and AGC circuit is incorporated thereto so that the timer 2 is assured to operate one time for each appearance of the sphygmus wave as shown at E irrespective of whether a person whose sphygmus wave is large or a person whose sphygmus wave is small.

Figure 6:
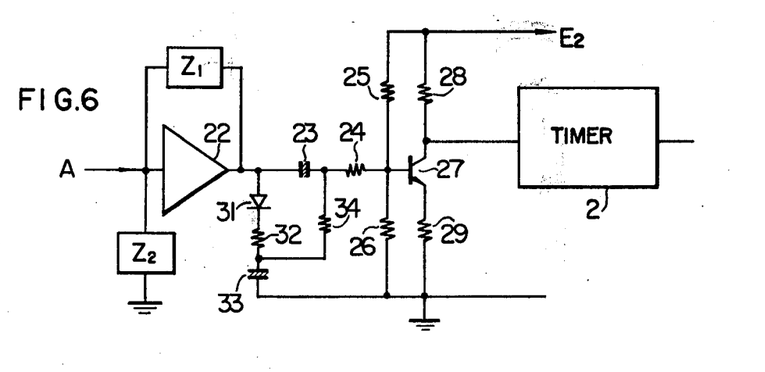
FIG. 6 shows a circuit diagram of a modified filter circuit incorporating an AGC circuit used in the present invention.

FIG. 6 shows the modified filter circuit incorporating AGC circuit in which a sphygmus wave input terminal A corresponds to the input terminal A shown in FIG. 1. A shaper 22 together with impedance elements $Z_1$ and $Z_2$ functions as a filter circuit for passing the sphygmus wave ranging from 5 to 30 Hz. The sphygmus wave is at the same time shaped into inverted form by a shaper 22, an output of which is passed through a coupling capacitor 23 and a resistor 24 and applied to a base of a transistor 27 which is normally biased in conducting state via resistors 25 and 26. The transistor 27 generates a pulse by a rise of the sphygmus wave. The numeral 28 designates a collector resistor for the transistor 27 and 29 designates an emitter resistor for the transistor 27. The collector of the transistor 27 is connected to a timer circuit 2 which converts the sphygmus wave to a single gate signal. The timer circuit 2 is identical to the timer circuit 2 shown in FIG. 1.

The output of the shaper 22, on the other hand, is coupled through a diode 31 and a resistor 32 to a capacitor 33 to store therein a charge which is proportional to the amplitude of the output of the shaper 22. The charge is used to bias the junction of the capacitor 23 and the resistor 24 through a resistor 34 to form a so-called AGC circuit.

With such system, when the sphygmus wave is extremely large, the charge stored in the capacitor 33 increases so that a larger input than determined by the bias determined by the resistors 25 and 26 is required for the transistor 27 to be operated. When convulsion of muscles is occuring, a charge for cancelling the waveform caused thereby is stored in the capacitor 33 to stabilize the operation of the transistor 27 and to prevent the signal from being transmitted to the timer circuit 2 for a period other than the sphygmus wave occuring period.

Figure 7:
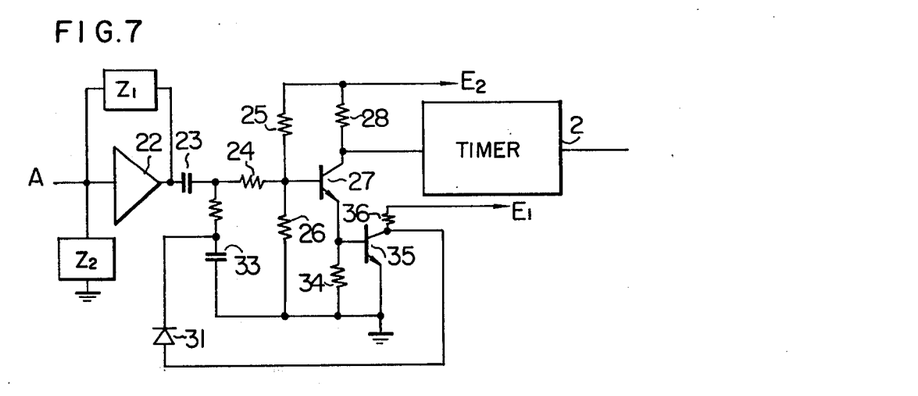
FIG. 7 shows a circuit diagram of another modified filter circuit.

FIG. 7 shows further embodiment of the present invention. The circuit of FIG. 7 is similar to that of FIG. 6 except that an additional transistor 35 is provided which is driven by a separate voltage supply $E_1$. When the transistor is non-conductive the transistor 35 is also non-conductive and the capacitor 33 is charged from the voltage supply $E_1$ through the resistor 36 and the diode 31. As a result, like in the circuit of FIG. 6, when the sphygmus wave input is large, the non-conduction period of the transistor 27 becomes longer so that the charge of the capacitor 33 increases and the input operating voltage of the transistor 27 rises. In this manner AGC operation is performed.

The circuit arrangement of FIG. 7 is advantageous to that of FIG. 6 as described hereinafter. Referring to FIG. 6, the capacitor is charged from a positive voltage of the output of the shaper 22 and thus the transistor 27 is activated by a negative voltage. Thus, where the output of the filter circuit element 22, $Z_1$, $Z_2$ is of unsymmetrical waveform, the effect of the AGC is not necessary assured. In contrast in the circuit arrangement of FIG. 7, since the capacitor 33 is charged at those time periods when the transistor 27 is not conducting, the AGC effect is assured even where the waveform of the output is unsymmetrical.

As described above, by the addition of a simple circuit the electrical blood pressure measuring apparatus of the present invention can produce one gate pulse in an expected sphygmus wave occuring period by the timer circuit so that the noise separation period can be minimized.

The sphygmus wave timer circuit 2 will now be further explained. Since the signal of the filter 3 is accepted by the timer 4 only during the operating period of the timer circuit 2, the operating period of the timer 2 is preferably short for better noise separation. However, as described previously, since the sphygmus wave is used to determine the presence or absence of the Korotkoff sounds, the operating period of the timer circuit 2 is preferably long in order to assure that one clock signal is generated for each pulsation and to prevent erroneous operation caused by noise. In order to satisfy these two contrary objects, the present invention uses two separate timer circuits. One embodiment thereof is explained with reference to FIGS. 8A and 8B.

Figure 8A:
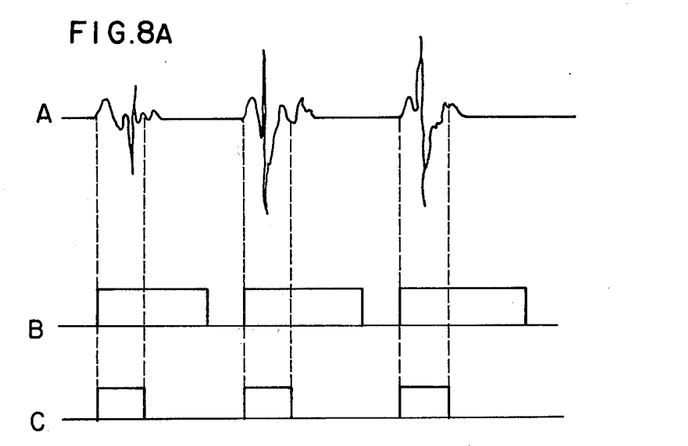
FIG. 8A shows a waveform derived at a microphone output and waveforms of timers.
Figure 8B:
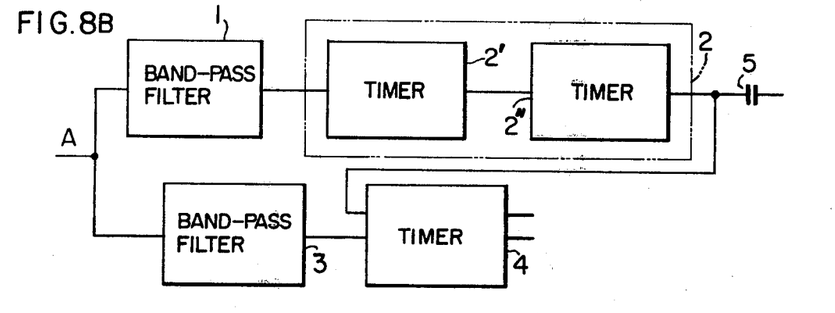
FIG. 8B shows partially a block diagram of a timer portion which may be used in the embodiment of FIG. 1.

FIG. 8B shows, in particular, a portion of the timer 2 of FIG. 1 and in which the timer 2 is replaced by a cascade connection of a timer 2' and a timer 2''. The timer 2' has a long operation period and the timer 2'' has a short operation period which is activated by the rise of operation of the timer 2'.

Referring to FIG. 8A at A there is shown a signal waveform picked up from a normal person by a microphone and corresponds to the input A shown in FIG. 1. In the waveform A the Korotkoff sounds are superimposed on a low frequency sphygmus wave. Waveforms B and C are diagram representations based on the waveform A. The waveform B of the timer 2' having a long operating period (200 to 600 m sec) is produced at the rise of the sphygmus wave A. The waveform C of the timer 2'' having a short operating period (50 to 300 m sec) is produced at the rise of the waveform B. The detection of the Korotkoff sound signal is permitted only during the operating period of the waveform C.

Thus, by the use of the two timers 2' and 2'' connected in series, it is possible to provide a sufficiently long time period by the timer 2' so that one signal is surely obtained for each sphygmus wave, and on the other hand by making the operation period of the timer 2'' to be short enough within the duration of the Korotkoff sounds, noise separation is effectively achieved by eliminating the signals occuring outside the operation period of the timer 2''.

Figure 9:
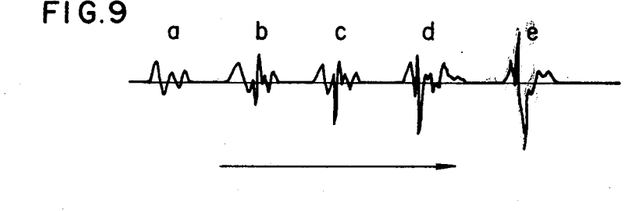
FIGS. 9 and 10 show the waveforms derived at the microphone output at the time of maximum blood pressure measurement and at the time of minimum blood pressure measurement.
Figure 10:
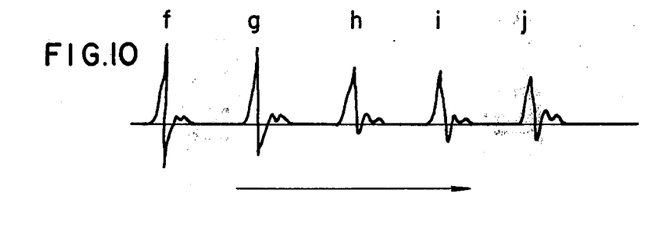

The filter 3 for detecting the Korotkoff sounds and the timer circuit 4 operated thereby will now be explained. The signal produced at the input A of FIG. 1 is an output from the microphone inserted in the cuff. At the time of the maximum blood pressure the waveform as shown in FIG. 9 is generated while at the time of the minimum blood pressure the waveform as shown in FIG. 10 is generated. The frequency components which superimpose on the sphygmus wave are different in FIGS. 9 and 10.

Referring to FIG. 9, the Korotkoff sounds are generated at $b$ superimposed on the sphygmus wave. At this point, the amplitude of the Korotkoff sounds is small.

Although the frequency components extend from 30 to 100 Hz, the main components occupy the range of 30 to 50 Hz. As the waveforms change from c to e they include larger signal components of 50 to 100 Hz. Therefore, in measuring the maximum blood pressure using the detecting cuff it is preferable to detect the Korotkoff sounds by passing them to a filter which passes only the frequency components of 30 to 100 Hz because higher S/N ratio is obtained.

FIG. 10 shows a microphone signal obtained in the vicinity of the minimum blood pressure in which the Korotkoff sounds diminish gradually. From f to g, a signal of 30 to 100 Hz is obtained as the Korotkoff sounds. However, at h and i, only such a signal of below 40 Hz is obtained and thereafter only the sphygmus wave signal is contained. An auscultator can detect the sounds as far as at g, and in view of the correspondence to the auscultatory method, it is required to detect the Korotkoff sounds as far as at g. In this respect, for use as a filter circuit for the minimum blood pressure, the filter circuit is designed to pass signals above 50 Hz. Without such filtering of signals, the results will not correspond to that obtained by the auscultatory method. On the other hand, if a band-pass filter of 30 to 100 Hz is used in order to assure the detection of the maximum blood pressure, the minimum blood pressure obtained would show too low.

In the present embodiment, in order to eliminate such inconvenience, two different filters and a resettable timer are used to selectively use the filters so as to maintain closer correspondence to the auscultatory method.

Figure 11:
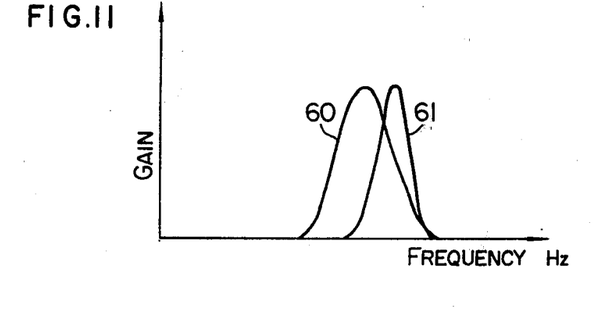
FIG. 11 shows characteristic of filters used in the embodiment of the present invention.

The correspondence of the results to those by the auscultatory method at the minimum blood pressure point is improved by the use of two filters of different characteristic shown in FIG. 11. In FIG. 11, the abscissa represents a frequency and the ordinate represents a gain, and 60 represents a characteristic of a filter used in detecting the maximum blood pressure while 61 represents a characteristic of a filter used in detecting the minimum blood pressure, which filter allows to pass only the frequency components of 50 to 100 Hz. By the use of the filter 61, the waveforms shown in FIG. 10 can produce an output which attenuates to correspond to that obtained by the auscultatory method and which is not affected by voice components of human beings which range above 100 Hz.

Figure 12:
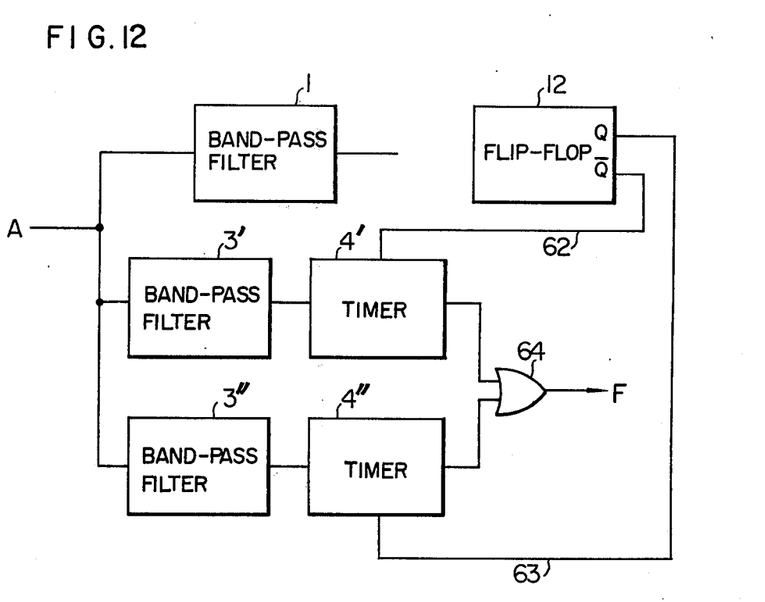
FIG. 12 illustrate a manner to select one of the two filters used in the embodiment of the present invention.

A method of switching the two filters is now explained in connection with FIG. 12. In FIG. 12, 3′, 3″ and 4′, 4″ designate halves of the circuits 3 and 4, respectively, shown in FIG. 1. The Korotkoff sound input A derived from the microphone is passed to the filter 3′ which passes the frequency components of 30 – 100 Hz, to activate the resettable timer circuit 4′. On the other hand, the input A is passed to the filter 3″ which passes the frequency components of 50 to 100 Hz, to activate the resettable timer circuit 4″. The numeral 12 designates a circuit for producing signal for identifying the maximum blood pressure, which, before the maximum blood pressure is identified, enables the operation of the timer circuit 4′ through a line 62 and applies a reset input to the timer circuit 4″ through a line 63 to stop the operation of the timer circuit 4″. After the maximum blood pressure has been identified, it applies a reset input to the timer circuit 4′ through the line 62 and removes the reset input on the line 63 to start the operation of the timer circuit 4″ for detecting the Korotkoff sounds. The outputs of the timer circuits 4′ and 4″ and applied to inputs of an OR gate 64, an output of which is used as the output F of the circuit 4 shown in FIG. 1.

In this manner, by the use of the resettable timer circuits, the present system allows exact correspondence to the auscultatory method of the point at which the Korotkoff sounds appear (maximum blood pressure point) and the point at which the Korotkoff sounds disappear (minimum blood pressure point), whereby more accurate measurement of the blood pressure is assured.

What is claimed is:

1. A blood pressure measuring apparatus wherein the Korotkoff sounds are detected by a microphone in association with a pump and a cuff, and the Korotkoff sounds are utilized to indicate maximum and minimum blood pressures, said apparatus comprising:

first band-pass filter means connected to said microphone to pass frequency components of sphygmus sounds;

second band-pass filter means connected to said microphone to pass frequency components of the Korotkoff sounds;

first timer means connected to said first band-pass filter means to produce a first rectangular wave signal in response to an output signal of said first filter means, said firsst rectangular wave signal having a predetermined time which substantially covers a sphygmus wave duration;

second timer means connected to said second filter means and to said first timer means to produce a second rectangular wave signal in response to an output signal of said second filter means, said second retangular wave signal having a timer width not shorter than the time width of said first rectangular wave signal;

clock signal generating means connected to said first timer means for generating a clock signal in response to a fall of each said first rectangular wave signal;

counter means connected to said second timer means and said clock signal generating means for reading the presence or absence of said second rectangular wave signal and for storing said second rectangular wave signal sequentially in accordance with said clock signal; and event determining means connected to said counter means for determining the occurrence of the maximum and minimum blood pressure events and for producing output signals representing the occurrence of said blood pressure events, said event determining means including:

maximum blood pressure determining means coupled to said counter means for producing an output signal representing the occurrence of a maximum blood pressure event only after said counter has counted at least two successive outputs of said second timer means in synchronism with said clock signal, and mimimum blood pressure determining means coupled to said counter means for producing an output signal representing the occurrence of a minimum blood pressure event only when said counter means has counted less than two successive outputs of said second timer means in synchronism with said clock signal and only after the occurrence of said maximum blood pressure event.

2. A blood pressure measuring apparatus according to claim 1, wherein said first band-pass filter means comprises
- a filter circuit element having an input terminal to receive the output of said microphone,
- a pulse generating circuit connected between said filter circuit element and said first timer means for generating a pulse signal upon activation by a rise of the sphygmus wave applied through said filter circuit element, and
- a bias means including an electric charge storing circuit having an input terminal connected to said filter circuit element and having an output terminal connected to said pulse generating circuit, said bias means storing an electric charge in proportion to an amplitude of the sphygmus wave and applying a bias potential to said pulse generating circuit corresponding to the amount of electric charge stored, thereby to obtain a single square pulse from said timer irrespective of the intensity of the sphygmus wave.

3. A blood pressure measuring apparatus according to claim 1, wherein said first timer means comprises a third timer and a fourth timer connected in series, said third timer being activated simultaneously with a rise of a sphygmus wave applied through said first band-pass filter means and having an operation period of 200 to 500 m sec, said fourth timer being activated at the operation starting time of said third timer and having an operation period of 50 to 300 m sec, and wherein said operation period of said fourth timer is used as an operation period for detecting the Korotkoff sounds.

4. A blood pressure measuring apparatus according to claim 1, wherein said first band-pass filter means has a frequency range of 5 to 30 Hz, and said second band-pass filter has a frequency range of 40 to 200 Hz.

5. A blood pressure measuring apparatus according to claim 1, wherein said second timer means is further provided with a gate or a reset terminal connected to said first timer means to use the output signal thereof as a gate or a reset signal thereby to enable said second timer means to accept the output signal of said second filter means only during the existence of the output signal of said first timer means.

6. A blood pressure measuring apparatus according to claim 1, wherein said second filter means comprises third and fourth filters connected in parallel with each other, said third filter having a frequency pass band of 30 to 100 Hz to detect the Korotkoff sounds in the case of the maximum blood pressure measurement and said fourth filter having a frequency pass band of 50 to 100 Hz to detect the Korotkoff sounds in the case of the minimum blood pressure measurement.

7. A blood pressure measuring apparatus according to claim 6, further comprising:
- third and fourth timers, each for forming the Korotkoff sound signal into a rectangular wave signal, respectively connected to said third and fourth filters;
- wherein said event determining means further includes switching means coupled to said third and fourth timers for enabling said third timer to generate an output signal prior to determination of said maximum blood pressure event and for enabling said fourth timer to generate a further output signal after the determination of said maximum blood pressure event.

8. A blood pressure measuring apparatus according to claim 7, wherein said switching means further inhibits operation of said fourth timer prior to the determination of said maximum blood pressure event and inhibits operation of said third timer after the determination of said maximum blood pressure event.

* * * * *